US012678071B2

(12) United States Patent
Chae et al.

(10) Patent No.: US 12,678,071 B2
(45) Date of Patent: Jul. 14, 2026

(54) CONTINUOUS BLOOD GLUCOSE MEASUREMENT APPARATUS

(71) Applicant: I-SENS, INC., Seoul (KR)

(72) Inventors: Kyoung Chul Chae, Seoul (KR); Hyun Ho Choi, Seoul (KR); Young Jea Kang, Seoul (KR); David Lee, Seoul (KR); Su Jin Lee, Seoul (KR)

(73) Assignee: I-SENS, INC., Seoul (KR)

( * ) Notice: Subject to any disclaimer, the term of this patent is extended or adjusted under 35 U.S.C. 154(b) by 817 days.

(21) Appl. No.: 17/908,913

(22) PCT Filed: Mar. 2, 2021

(86) PCT No.: PCT/KR2021/002538
§ 371 (c)(1),
(2) Date: Sep. 2, 2022

(87) PCT Pub. No.: WO2021/177687
PCT Pub. Date: Sep. 10, 2021

(65) Prior Publication Data
US 2024/0215870 A1 Jul. 4, 2024

(30) Foreign Application Priority Data

Mar. 3, 2020 (KR) ........................ 10-2020-0026665

(51) Int. Cl.
*A61B 5/145* (2006.01)
*A61B 5/00* (2006.01)
(52) U.S. Cl.
CPC ...... *A61B 5/14532* (2013.01); *A61B 5/14503* (2013.01); *A61B 5/6849* (2013.01)
(58) Field of Classification Search
CPC ............ A61B 5/14532; A61B 5/14503; A61B 5/6848; A61B 5/150022; A61B 5/150427; A61B 5/1473
See application file for complete search history.

(56) References Cited

U.S. PATENT DOCUMENTS 6,809,653 B1 * 10/2004 Mann ................... A61B 5/0002
604/506
6,936,006 B2 8/2005 Sabra
(Continued)

FOREIGN PATENT DOCUMENTS

JP      2005-520648 A      7/2005
JP      2016-501070        1/2016
(Continued)

OTHER PUBLICATIONS

International Search Report for PCT/KR2021/002538 mailed on Jun. 9, 2021 and its English translation from WIPO (now published as WO 2021/177687).
(Continued)

*Primary Examiner* — Christian Jang
(74) *Attorney, Agent, or Firm* — WOMBLE BOND DICKINSON (US) LLP

(57) ABSTRACT

The present disclosure relates to a continuous blood glucose measurement device configured to prevent, in a state where a body attachment unit is inserted in and attached to a human body, an incision portion made by a guide needle from being formed to surround at least a part of a sensing area formed at a sensing member, whereby an incision portion is not formed around the sensing area so as to prevent the incision portion from causing a drop in a blood glucose measurement value and thus enable detection of an accurate blood glucose measurement value from the early stage of operation. Further, the guide needle has a shape not surrounding at least a part of the sensing area, so as to prevent, even without an additional device, the guide needle from forming an incision portion around the sensing area in a human body and thus enhance, by a simple structure, the accuracy of blood glucose measurement.

9 Claims, 10 Drawing Sheets

(a)

(b)

(56) References Cited

U.S. PATENT DOCUMENTS

| | | | |
|---|---|---|---|
| 7,727,147 B1 | 6/2010 | Osorio et al. | |
| 10,456,064 B2 | 10/2019 | Paterson et al. | |
| 2008/0064941 A1 | 3/2008 | Funderburk et al. | |
| 2012/0130209 A1 | 5/2012 | Bunge | |
| 2014/0135605 A1 | 5/2014 | Gottlieb et al. | |
| 2016/0030078 A1* | 2/2016 | Lee ...................... | A61B 5/6865 |
| | | | 606/182 |
| 2016/0058470 A1 | 3/2016 | Peterson et al. | |
| 2016/0058472 A1 | 3/2016 | Peterson et al. | |
| 2016/0331283 A1* | 11/2016 | Rao .................... | A61B 5/14503 |
| 2017/0079564 A1 | 3/2017 | Shah et al. | |
| 2017/0112534 A1* | 4/2017 | Schoonmaker .... | A61B 17/3468 |
| 2018/0235520 A1* | 8/2018 | Rao ...................... | A61B 5/6823 |

FOREIGN PATENT DOCUMENTS

| | | |
|---|---|---|
| JP | 2017-525516 | 9/2017 |
| KR | 10-1891309 | 8/2018 |
| KR | 10-2018-0132557 | 12/2018 |
| KR | 10-2019-0025208 | 3/2019 |
| WO | 2016/191302 | 12/2016 |
| WO | 2018/118061 | 6/2018 |
| WO | 2020/027423 | 2/2020 |

OTHER PUBLICATIONS

Written Opinion of the International Searching Authority for PCT/KR2021/002538 mailed on Jun. 9, 2021 and its English translation by Google Translate (now published as WO 2021/177687).

Extended European Search Report dated May 25, 2023 for European Patent Application No. 20 848 138.2.

Extended European Search Report dated Jan. 11, 2024 for European Patent Application No. 21764277.6.

Office Action dated Oct. 1, 2024 for Japanese Patent Application No. 2022-552911 and its English translation from Global Dossier.

Notice of Allowance Dated May 27, 2025 for Japanese Patent Application No. 2022-552911 and its English translation from Global Dossier.

Notice of Allowance dated May 25, 2026 for Chinese Patent Application No. 202180017164.3 and its English translation by Google Translate.

* cited by examiner

[Fig. 1]
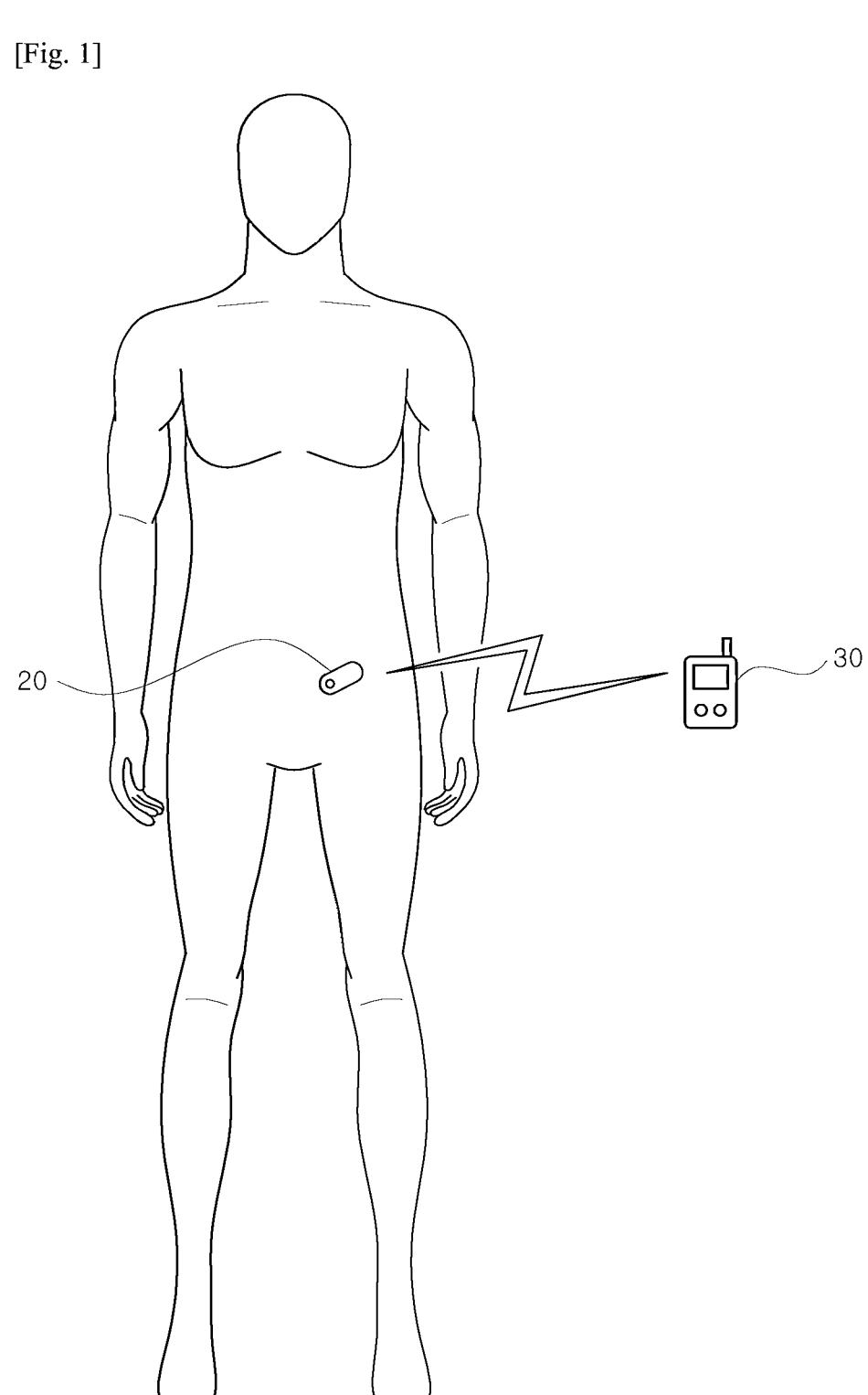

[Fig. 2]
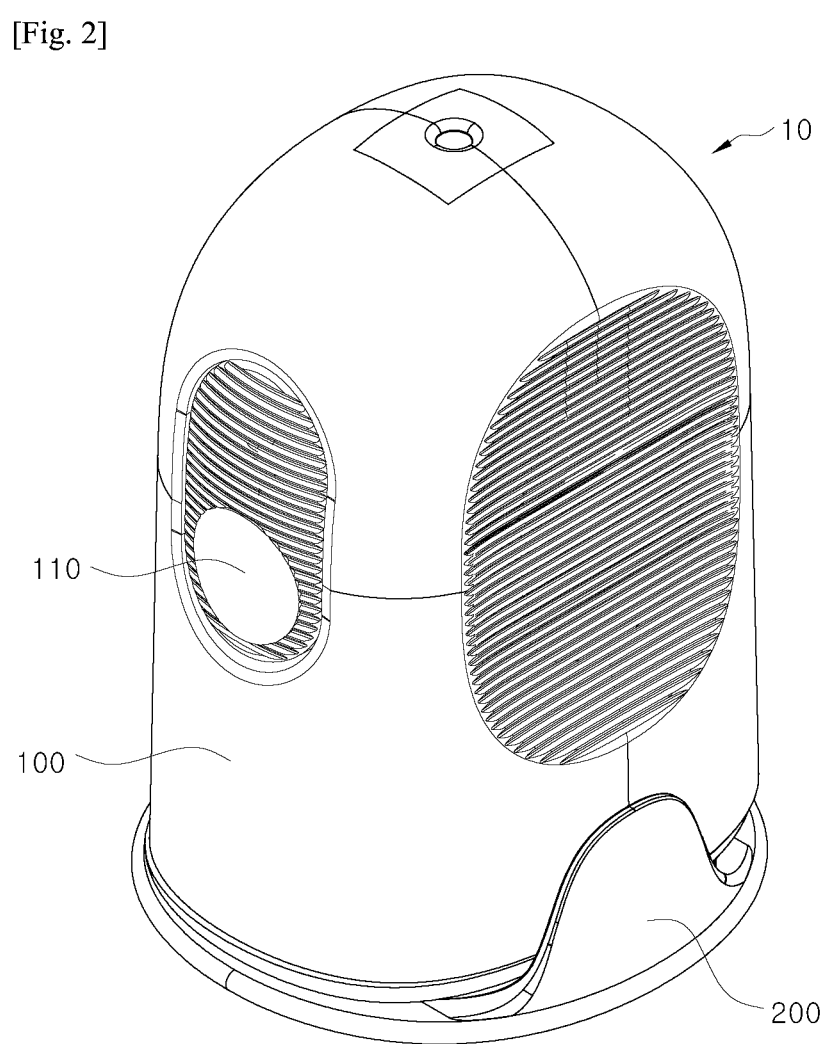

[Fig. 3]
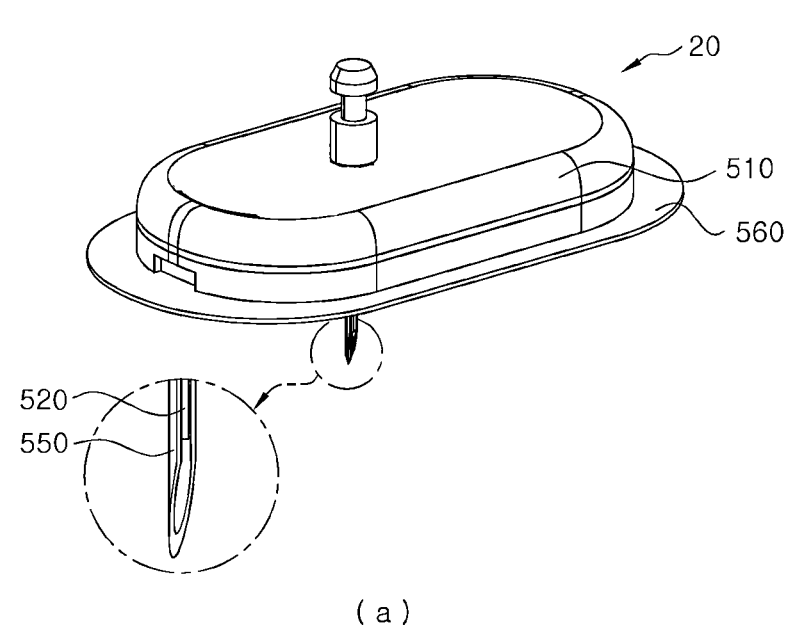
( a )
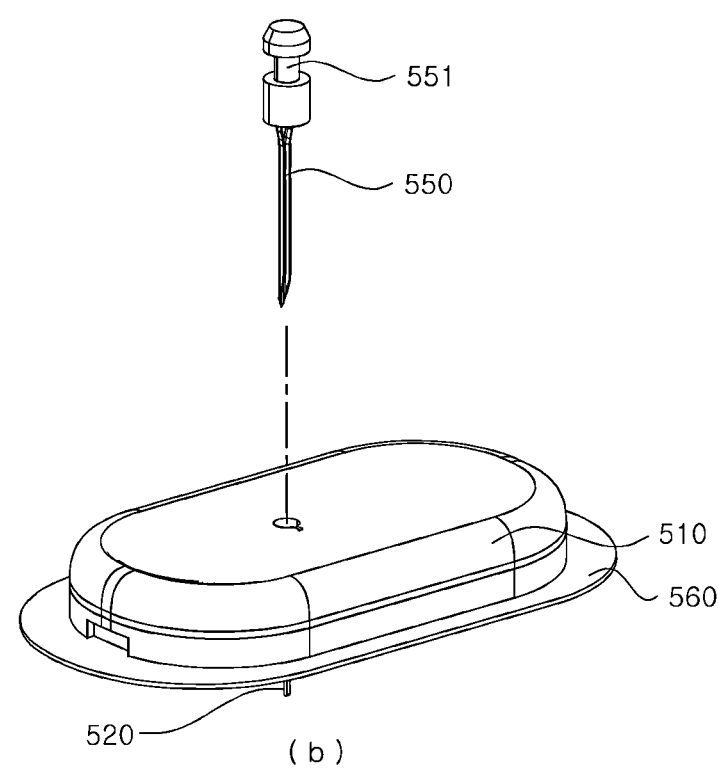
( b )

[Fig. 4]

[Fig. 5]
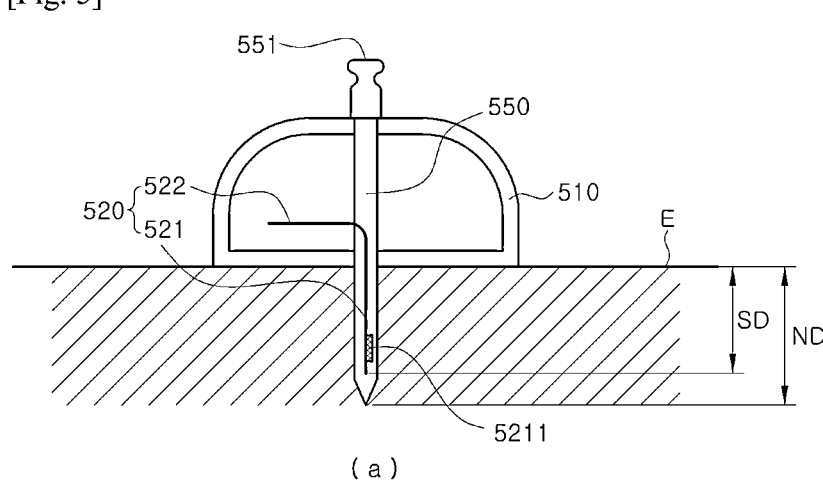
( a )
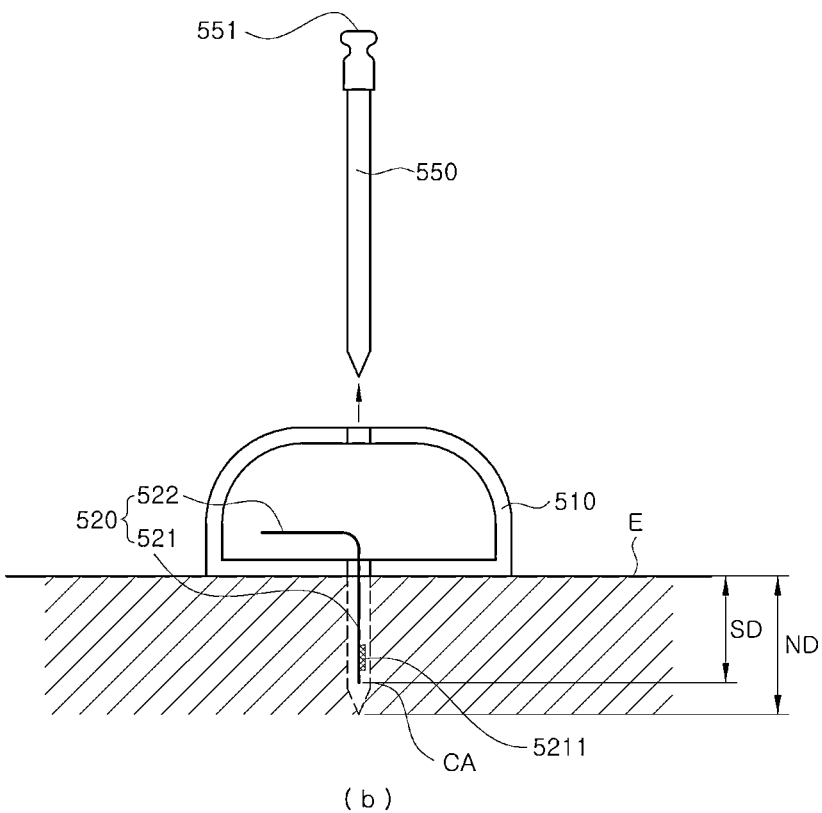
( b )

[Fig. 6]

[Fig. 7]
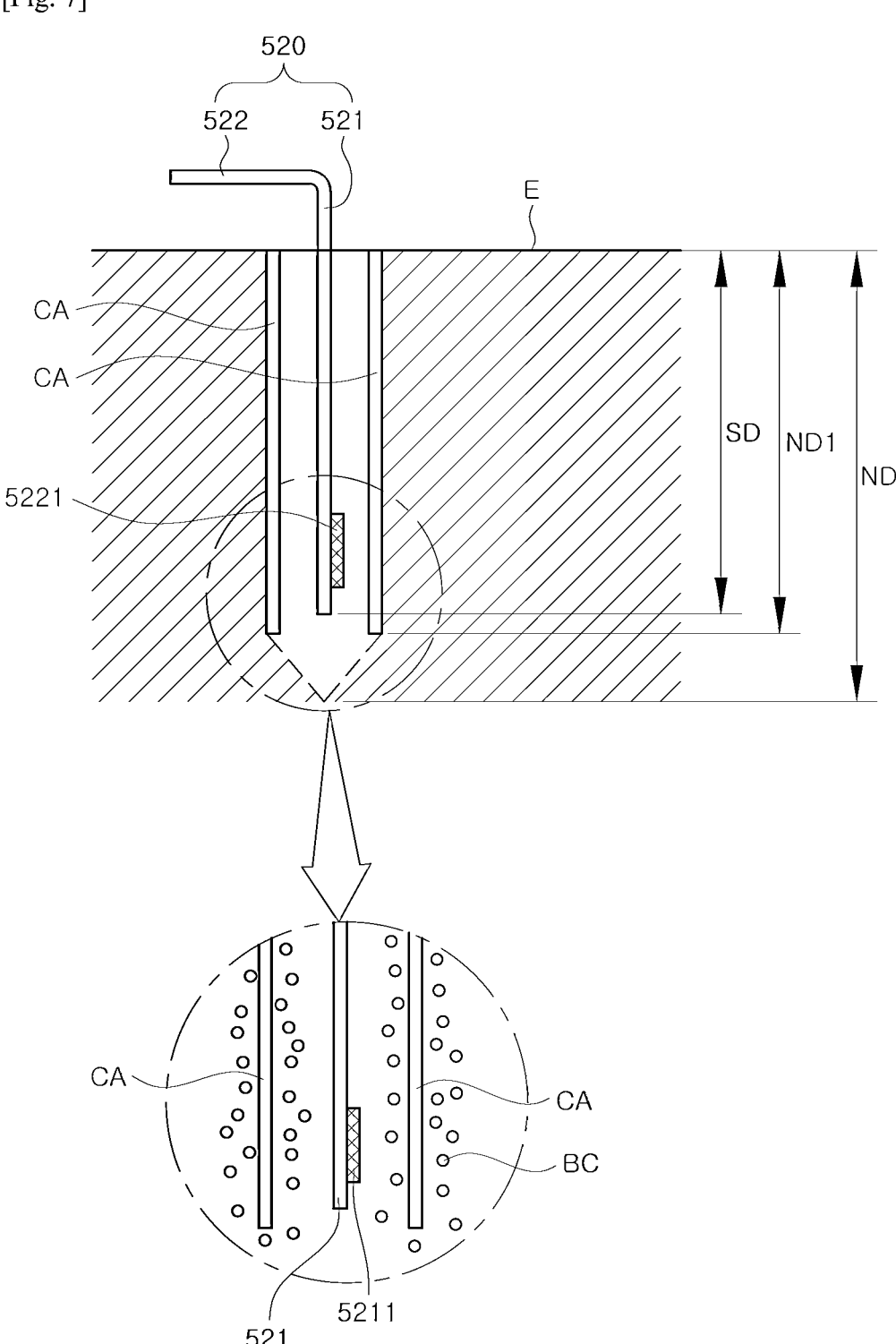

[Fig. 8]
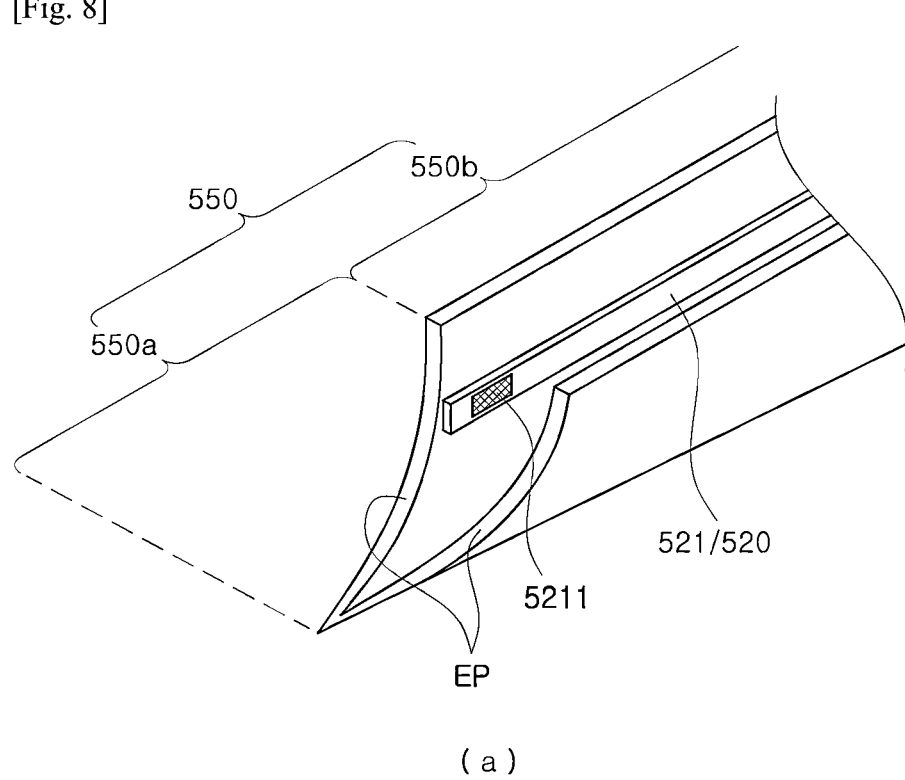
( a )
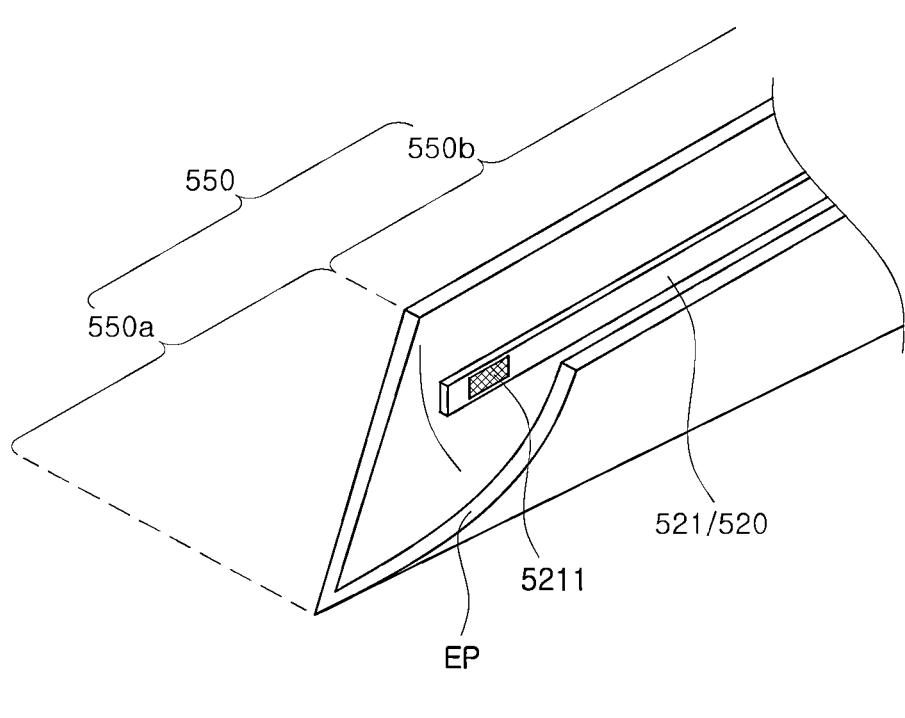
( b )

[Fig. 9]
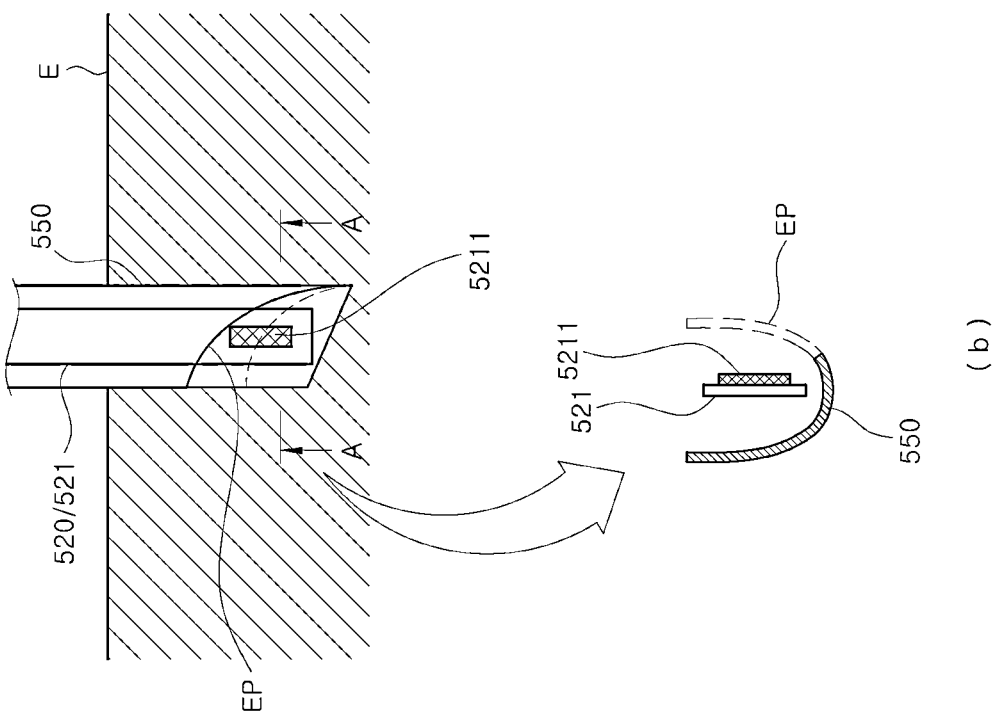
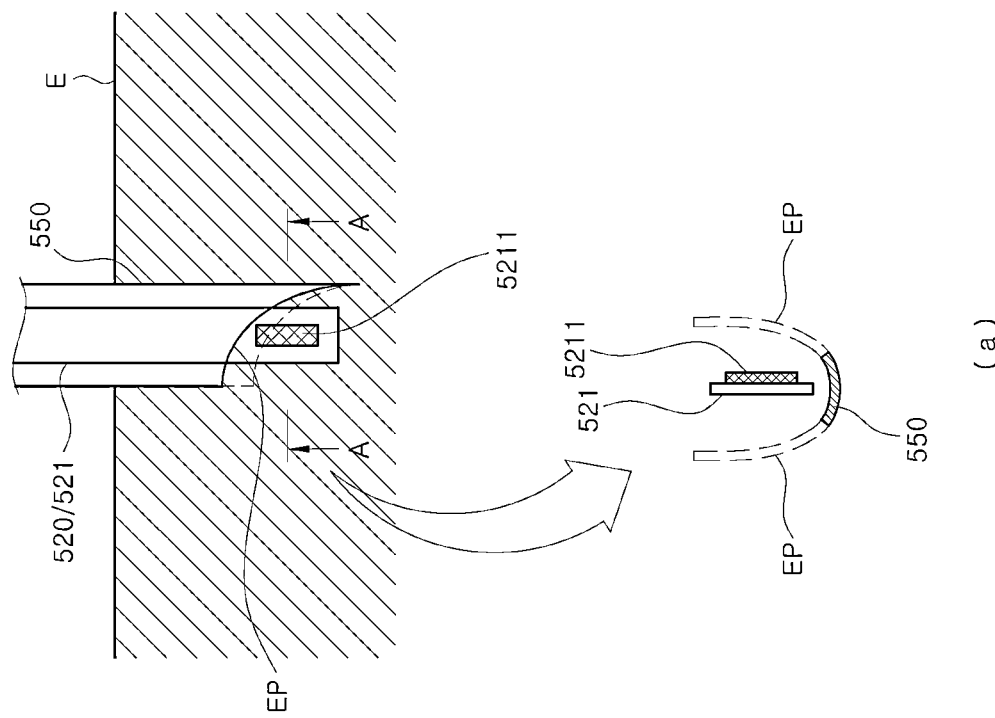

[Fig. 10]
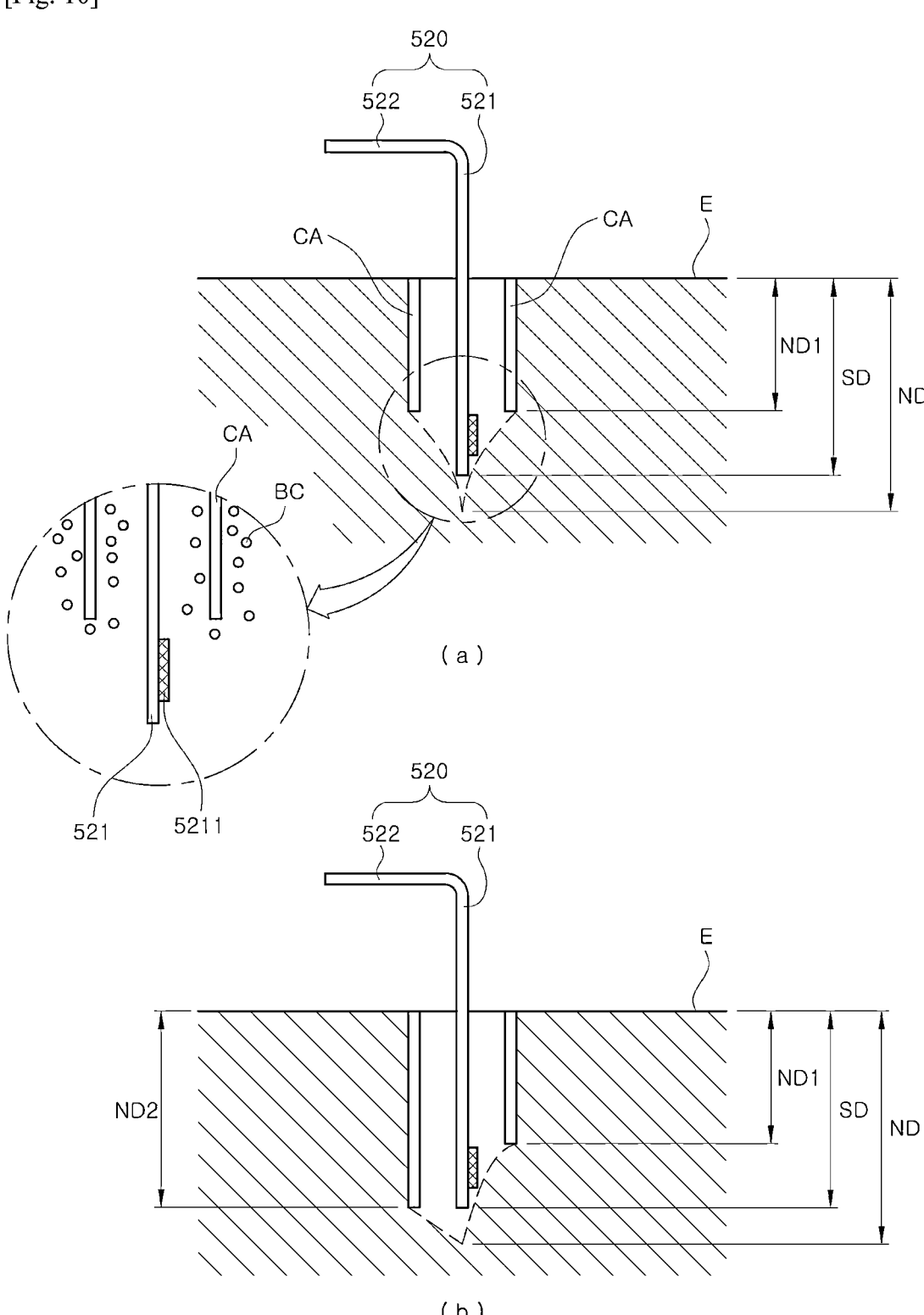
( a )
( b )

CONTINUOUS BLOOD GLUCOSE MEASUREMENT APPARATUS

CROSS-REFERENCE TO RELATED APPLICATIONS

The present application is the U.S. National Phase of PCT Application No. PCT/KR2021/002538 filed on Mar. 2, 2021, which claims the priority to Korean Patent Application No. 10-2020-0026665 filed on Mar. 3, 2020, the entire contents of which are incorporated herein by reference.

TECHNICAL FIELD

The present disclosure relates to a continuous blood glucose measurement apparatus. More specifically, the present disclosure relates to a continuous blood glucose measurement apparatus in which, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, accordingly a phenomenon of lowering a blood glucose measurement value caused by the incised portion can be prevented, thereby detecting an accurate blood glucose measurement value from the early stage of operation, and by a shape of the guide needle not covering at least a partial area of the sensing area, the incised portion of the guide needle in the body does not form around the sensing area without a separate and additional device, thereby improving a blood glucose measurement accuracy with a simple structure.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. Cygnus Corporation, Redwood City, Calif., U.S.A, has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module inserted and attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, and an adhesive tape is attached to an outer housing of the sensor module so that the sensor module can be attached to the human body. If the sensor module is attached to the human body skin through the applicator according to this structure, a state that the sensor module is attached to the human body skin is maintained by the adhesive tape, and, the blood glucose is periodically and continuously measured in this state.

Because a part inserted into the skin among a sensor member of the sensor module is formed of a soft material, a guide needle is provided to guide the process of inserting the sensor member into the skin. That is, the part inserted to the skin among the sensor member is arranged to outwardly protrude from the bottom surface of an outer housing of the sensor module, the guide needle is arranged to surround a part of the sensor member inserted into the skin from the outside, and, during the process in which the sensor module is attached to the skin through the applicator, the guide needle is inserted into the skin together with the sensor member. When the skin insertion process of the sensor member is completed, the guide needle is configured to be removed from the skin by the applicator.

Such a continuous blood glucose measurement apparatus generally exhibits a characteristic that, when the sensor module is attached to the body, the blood glucose measurement accuracy is lowered in the initial state of operation, and, after a considerable amount of time has elapsed, the accuracy is improved. Although various studies are being conducted to solve the problem of the deterioration of the initial measurement accuracy, there are still no satisfactory research results.

SUMMARY

Technical Problem

The present disclosure is invented to solve problems in conventional technique, and the purpose of the present disclosure is for providing a continuous blood glucose measurement apparatus in which, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, and accordingly a phenomenon of lowering a blood glucose measurement value caused by the incised portion can be prevented, thereby detecting an accurate blood glucose measurement value from the early stage of operation.

Another purpose of the present disclosure is for providing a continuous blood glucose measurement apparatus in which, by a shape of the guide needle not covering at least a partial area of the sensing area, the incised portion of the guide needle in the body does not form around the sensing area without a separate and additional device, thereby improving a blood glucose measurement accuracy with a simple structure.

Solution to Problem

The present disclosure provides a continuous glucose measurement apparatus comprising: a body attachable unit configured to be insertedly attachable to a body by an applicator and periodically measure blood glucose; and wherein the body attachable unit comprises: a sensor module configured to be insertable to the body, wherein a sensing area to react with the blood glucose in the body is formed at one side of the sensor module, and a guide needle arranged to cover an outside of at least a partial area of the sensor module to guide insertion of the sensor module to the body and configured to, after linearly moving integrally together with the sensor module, be extracted and removed from the body, wherein an end of the guide needle is arranged to protrude further than an end of the sensor module toward a body insertion direction or protrude as much as the end of the sensor module, and the guide needle is formed to have a shape of not covering an outside of at least a partial area of the sensing area.

At this time, the sensor module may comprise a sensor probe portion formed to be elongated along the body insertion direction so that at least a partial section of the sensor probe portion is insertable into the body, and the sensing area may be formed at an end part of the sensor probe portion.

Additionally, the guide needle may be formed to have a shape of covering an outside of the sensor probe portion, and an opening may be formed at an end portion of the guide needle not to cover the at least a partial area of the sensing area of the sensor module.

Further, the opening of the guide needle may be formed to have a shape of not surrounding an entire area of the sensing area.

In addition, the opening of the guide needle may be formed to have a shape of not covering a partial area of the sensing area.

Additionally, the sensor probe portion may be formed to have a plate shape elongated along the body insertion direction, the sensing area may be formed at one surface of the sensor probe portion, and the opening of the guide needle may be formed to have an opened shape in which an area of the guide needle facing the one surface of the sensor probe portion at which the sensing area is formed is opened.

Further, the guide needle may comprise: an incision portion formed at a front end portion of the guide needle to incise skin of the body in a process in which the guide needle is being inserted into the body, and an insertion support portion formed to be extended from a back portion of the incision portion and configured to be inserted to the body continuously along the incised portion incised by the incision portion, and the opening may be formed at an area of the incision portion.

Advantageous Effects of Invention

According to an embodiment of the present disclosure, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, and accordingly a phenomenon of lowering a blood glucose measurement value caused by the incised portion can be prevented, thereby detecting an accurate blood glucose measurement value from the early stage of operation.

According to an embodiment of the present disclosure, by a shape of the guide needle not covering at least a partial area of the sensing area, the incised portion of the guide needle in the body does not form around the sensing area without a separate and additional device, thereby improving a blood glucose measurement accuracy with a simple structure.

BRIEF DESCRIPTION OF THE DRAWINGS

FIG. 1 is a diagram for schematically illustrating a basic system of a continuous blood glucose measurement apparatus according to an embodiment of the present disclosure.

FIG. 2 is a diagram for schematically illustrating a structure of an applicator of a continuous blood glucose measurement apparatus according to an embodiment of the present disclosure.

FIG. 3 is a diagram for schematically illustrating a body attachable unit of a continuous blood glucose measurement apparatus according to an embodiment of the present disclosure.

FIG. 4 is a diagram for schematically showing structures of a sensor module and a guide needle of a body attachable unit according to a first embodiment of the present embodiment.

FIG. 5 is a diagram for conceptually illustrating a body insertion and attachment process of a body attachable unit according to a first embodiment of the present disclosure.

FIG. 6 is a diagram for conceptually illustrating a body insertion structure of a sensor module and a guide needle according to a first embodiment of the present disclosure.

FIG. 7 is a diagram for conceptually illustrating an arrangement structure of a body incision portion formed by a guide needle and a sensor module according to a first embodiment of the present disclosure.

FIG. 8 is a diagram for schematically illustrating structures of a sensor module and a guide needle of a body attachable unit according to a second embodiment of the present disclosure.

FIG. 9 is a diagram for conceptually illustrating a body insertion form of a sensor module and a guide needle of a body attachable unit according to a second embodiment of the present disclosure.

FIG. 10 is a diagram for conceptually illustrating an arrangement form of a body incision portion formed by a guide needle and a sensor module according to a second embodiment of the present disclosure.

DETAILED DESCRIPTION OF EMBODIMENTS

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

FIG. 1 is a diagram for schematically illustrating a basic system of a continuous blood glucose measurement apparatus according to an embodiment of the present disclosure, FIG. 2 is a diagram for schematically illustrating a structure of an applicator of a continuous blood glucose measurement apparatus according to an embodiment of the present disclosure, and FIG. 3 is a diagram for schematically illustrating a body attachable unit of a continuous blood glucose measurement apparatus according to an embodiment of the present disclosure.

A continuous blood glucose measurement apparatus according to an embodiment of the present disclosure is configured to attach a body attachable unit (20) having a sensor module (520) insertable into a body using an applicator (10) for continuous blood glucose measurement, to insert and attach the body attachable unit (20) to the body by operating or manipulating the applicator (10) to periodically and continuously measure blood glucose from the body, and to transmit blood sugar measurement information periodically measured through the body attachable unit (20) to a separate terminal (30) to output it.

The body attachable unit (20) can be manufactured as a single unit product by being assembled inside the applicator (10), and, in this case, has a structure of which use method is very simple in a shape in which additional work of a user can be minimized when using the continuous blood glucose measurement apparatus. Of course, various manufacturing ways including an example that the body attachable unit (20) is supplied to the user separately from the applicator (10) and the user inserts the body attachable unit (20) into the inside of the applicator (10) to operate it can be implemented.

The body attachable unit (20) may be configured to be attachable to a human body to periodically measure blood sugar level or glucose by extracting body fluid, and transmit the blood glucose measurement result to an external device such as an external terminal (30) and so on. A sensor module (520) of which one end portion can be inserted into the human body and a wireless communication chip (not shown) configured to wirelessly communicate with the external terminal (30) can be disposed inside the body attachable unit (20).

The applicator (10) is formed such that the body attachable unit (20) is fixedly coupled to the inside of the applicator (10), and the applicator (10) is configured to outwardly discharge the body attachable unit (20) according to the user's pressurizing manipulation to a pressurizing button (110).

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, a sensor applicator assembly according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is supplied to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip, no connection with an extra transmitter is needed and therefore it can be used more conveniently.

A separate and additional protection cap (200) can be separably coupled to the applicator (10) in order to block external exposure in a state that the applicator (10) is inserted in the inside of the applicator (10), and it may be configured that the user can attach the body attachable unit

(20) to the human body by manipulating the applicator (10) after the protection cap (200) is separated and outwardly discharging the body attachable unit (20) toward a position where the protection cap (200) is removed.

In the embodiment of the present disclosure, an adhesive tape (560) is provided at a side of the body attachable unit (20) contacting the human body to be attached to the body, to protect the adhesive tape (560) a release paper (not shown) is attached to a surface of the adhesive tape (560) contacting the human body, and the release paper of the adhesive tape (560) may be configured to be separated and removed from the adhesive tape (560) during the operation of separating the protection cap (200) from the applicator (10).

In a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

In the body attachable unit (20), the sensor module (520) is disposed in a separate housing (510), and one end portion of the sensor module (520) outwardly protrudes from the bottom surface of the housing (510) so that it can be inserted and attached to the human body. The sensor module (520) may comprise a sensor probe module (521) (See FIG. 5) to be inserted into the human body, and a sensor body module (522) (See FIG. 5) disposed inside the housing (510), and the sensor probe module and the sensor body module are formed as one end portion and another end portion of the sensor unit (520), respectively, and in a bent shape.

In this embodiment, to smoothly perform the body insertion process of the sensor module (520), a separate guide needle (550) may be separatably coupled to the housing (510). The guide needle (550) may surround one end portion of the sensor module (520) and be configured to be inserted together with the sensor module (520) so that one end portion of the sensor module (520) can be stably inserted into the human body.

As shown in FIG. 2, the guide needle (550) may be separatably coupled to the housing (510) in a direction penetrating the top and bottom of the housing (510) of the body attachable unit (20), the guide needle (550) may be formed to have a structure covering the outside of the sensor module (520), and a need head (551) is formed at the upper end portion of the guide needle (550). If the body attachable unit (20) is moved in the direction outwardly discharged by the applicator (10), the guide needle (550) is inserted into the human body first before the sensor module (520) is inserted into the human body and the guide needle (550) may guide the sensor module (520) such that the sensor module (520) can be stably inserted in the skin. The guide needle (550) may be coupled with a needle extracting means (not shown) of the applicator (10) through the needle head (551), and after the body attachable unit (20) is inserted and attached to the human body by the operation of the applicator (10), the guide needle (550) may be configured to be withdrew and removed from the human body by the needle extracting means of the applicator (10).

Next, the details of configurations of the sensor module (520) of the body attachable unit (20) and the guide needle (550) will be followed.

Figure 4:
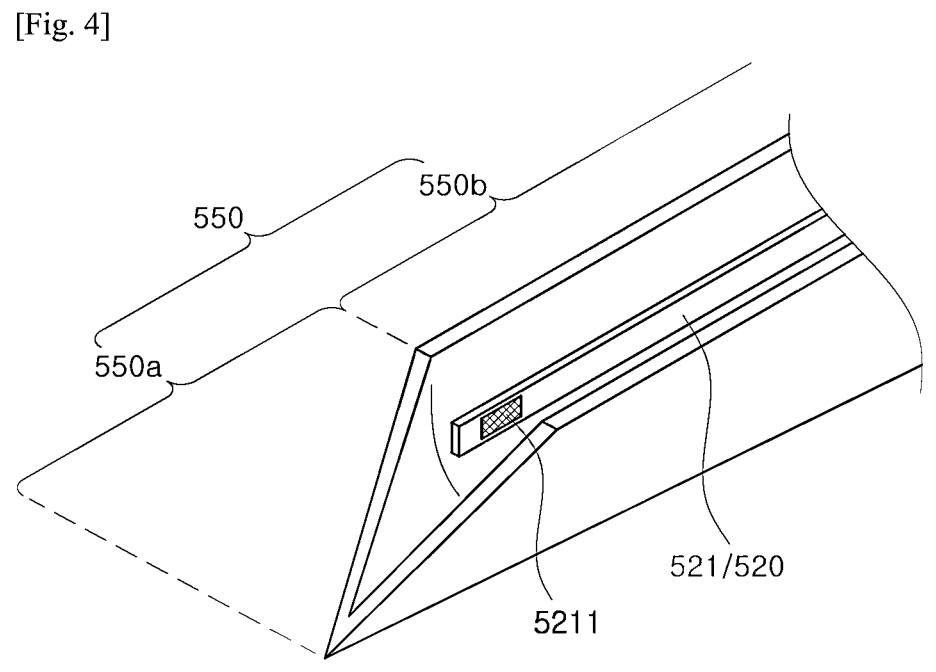
Figure 6:
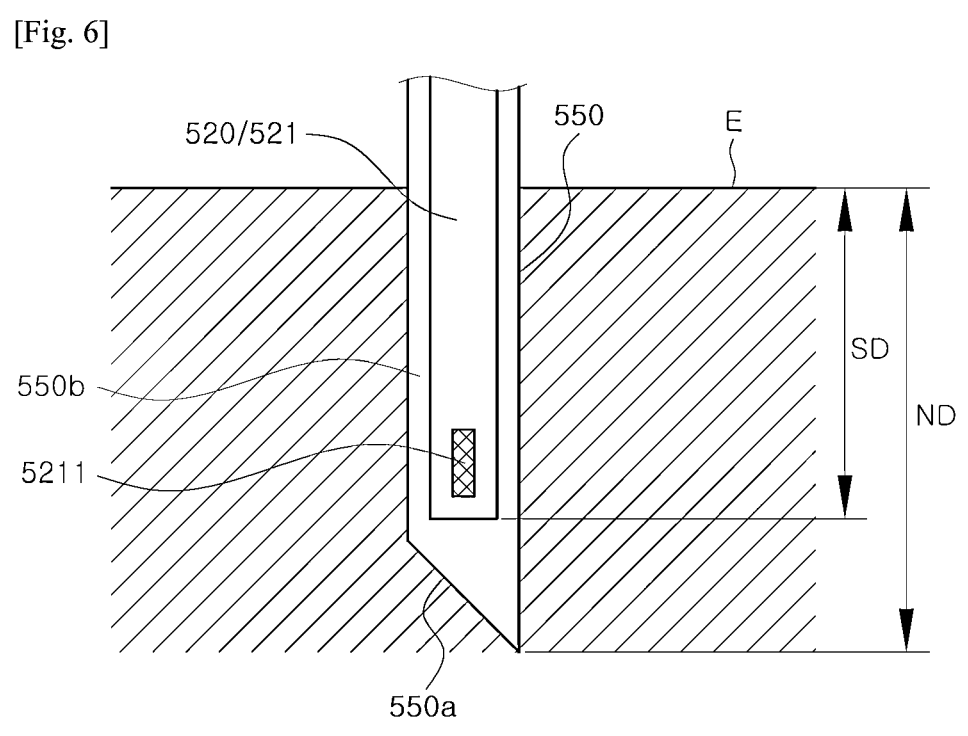

FIG. 4 is a diagram for schematically showing structures of a sensor module and a guide needle of a body attachable unit according to a first embodiment of the present embodiment, FIG. 5 is a diagram for conceptually illustrating a body insertion and attachment process of a body attachable unit according to a first embodiment of the present disclosure, FIG. 6 is a diagram for conceptually illustrating a body insertion structure of a sensor module and a guide needle according to a first embodiment of the present disclosure, and FIG. 7 is a diagram for conceptually illustrating an arrangement structure of a body incision portion formed by a guide needle and a sensor module according to a first embodiment of the present disclosure.

As described above, the sensor module (520) of the body attachable unit (10) comprises a sensor body portion (522) disposed inside the housing (510), and a sensor probe portion (521) bent downward from the sensor body portion (522) and protruded downwardly toward the lower portion of the housing (510). The sensor probe portion (521) is formed to be elongated along a body insertion direction so that at least a part of the sensor probe portion (521) can be inserted into the body, and a sensing area (5211) reacting to blood glucose is formed at an end portion of the sensor probe portion (521) to measure blood glucose in the body. The blood glucose in the body is measured by converting the degree of reaction with blood glucose into an electrical signal through the sensing area (5211) and analyzing it to measure the blood glucose in the body.

The sensor probe portion (521) may be formed in a flat plate shape as shown in FIG. 4, and the sensing area (5211) may be formed on one surface of the sensor probe portion (521) of a flat plate structure.

The guide needle (550) is formed in a shape that surrounds the outside of the sensor probe portion (521), and one side of the guide needle (550) may be formed in a "ㄷ" character channel shape open along a longitudinal direction. Of course, the shape of the guide needle (550) may be formed in the structure which can be various shapes of hollow pipes in which some regions are opened along a longitudinal direction.

The guide needle (550) is configured to guide the insertion of the sensor module (520) into the body and is inserted into the body and incises the body skin before the sensor module (520) is inserted in the process of the guide needle's being inserted into the body together with the sensor module (520), an incision portion (550a) is formed at a front end portion of the guide needle (550) and in a structure which can incise the body skin while being inserted into the body, and a insertion support portion (550b) which is continuously inserted into the body along a portion incised by the incision portion (550a) is extendedly formed at a rear portion of the incision portion (550a). The insertion support portion (550b) of the guide needle (550) is arrange to surround an outside of the sensor probe portion (521) of the sensor module (520), and the sensing area (5211) formed at an end portion of the sensor probe portion (521) is also arranged such that an outside of the sensing region (5211) is surrounded by the insertion support portion (550b) of the guide needle (550).

As described above, the sensor module (520) and the guide needle (550) are coupled to the housing (510) and are inserted and attached to the body skin by the applicator (10), and after the sensor module (520) and the housing (510) are attached to the body skin, the guide needle (550) is drawn and removed from the body skin by the applicator (10).

At this time, as illustrated in FIG. 5(a), an insertion depth (ND) of the guide needle (550) is formed to be deeper than an insertion depth (SD) of the sensor module (520) according to the arrangement relationship of the sensor module (520) and the guide needle (550). Because the insertion support portion (550b) of the guide needle (550) is arranged to surround the sensor module (520), an insertion depth (ND) of an end of the incision portion (550a) of the guide needle (550) is also formed to be deeper than the insertion depth (SD) of the sensor module (520). The guide needle (550) incises body skin (E) and leaves cut in the body skin (E), and if the guide needle (550) is drawn and removed after the guide needle (550) is inserted into the body, the portion of the body skin (E) incised by the guide needle (550) has the same depth as the insertion depth (ND) of the guide needle (550).

In this way, when looking into details of the arrangement relationship between the portion incised by the guide needled (550) in the body skin (E) and the sensor module (520) after the guide needle (550) is drawn out and removed from the body skin (E), an incised portion (CA) by the guide needle (550) is formed to be spaced apart from both sides of the sensor module (520) based on a vertical cross-section of the body skin (E) as shown in FIG. 7. At this time, when the separation distance between the sensor module (520) and the guide needle (550) is very small or in a non-spaced contact state, the incised portion (CA) by the guide needle (550) in the body skin (E) may be formed in contact with the sensor module (520).

The incised portions (CA) formed on both sides of the sensor module (520) in the body skin (E), respectively, are substantially formed by inserting the insertion support portion (550b) of the guide needle (550), and the incised portion formed by the incision portion (550a) of the guide needle (550) may be formed to extend deeper in an oblique direction from the incised portion (CA) by the insertion support portion (550b) as illustrated by a dotted line in FIG. 7. The depth of the incised portion (CA) formed by the incision portion (550a) of the guide needle (550) is ND, the depth of the incised portion (CA) formed by the insertion support portion (550b) of the guide needle (550) is ND1, and in this case, the insertion depth of the sensor module (520) is SD.

Accordingly, around a peripheral portion of the sensing area (5211) formed on one surface of the sensor probe portion (521) of the sensor module (520), the incised portion (CA) formed by the insertion support portion (550b) of the guide needle (550) is formed in a structure of surrounding an outside of the sensing area (5211).

Because the incised portion (CA) formed by the guide needle (550) is a wound in the body, a small amount of bleeding occurs at the incised portion (CA) and at the same time, white blood cells (BC) due to the body's immune response are gathered to the incised portion (CA) as shown in the enlarged view of FIG. 7. As such, if the white blood cells (BC) are gathered into the incised portion (CA), the blood glucose response amount is changed in the sensing area (5211) of the sensor module (520) positioned nearby, thereby lowering blood glucose measurement accuracy.

Accordingly, when the white blood cells (BC) are gathered to the incised portion (CA) formed by the guide needle (550) after the guide needle (550) is withdrawn and removed, adjacent blood glucose substance (glucose) is coupled with the white blood cells (BC), and accordingly, the reaction amount of the blood glucose substance reacting with the sensing area (5211) may be reduced. As such, a blood glucose measurement value measured by the sensor module (520) is not a blood glucose measurement value which is in a normal state, but a substantially lowered value due to the reduction of the blood glucose substance reacting with the sensing area (5211) caused by the concentration of the white blood cells (BC). This change in the blood glucose measurement amount due to the influence of the white blood cells (BC) may continue for several days until all the incised portions (CA) are recovered.

Therefore, because the guide needle (550) is inserted into the body together with the sensor module (520), in the body attachable unit (10) of the continuous blood glucose measurement apparatus, a phenomenon in which the accuracy of blood glucose measurement is deteriorated due to the incised wound formed by the guide needle (550) at an initial stage operation of starting to attaching the body attachable unit (10) occurs.

Hereinafter, a structure for minimizing a phenomenon of decrease in blood glucose measurement accuracy described above will be described.

FIG. 8 is a diagram for schematically illustrating structures of a sensor module and a guide needle of a body attachable unit according to a second embodiment of the present disclosure, FIG. 9 is a diagram for conceptually illustrating a body insertion form of a sensor module and a guide needle of a body attachable unit according to a second embodiment of the present disclosure, and FIG. 10 is a diagram for conceptually illustrating an arrangement form of a body incision portion formed by a guide needle and a sensor module according to a second embodiment of the present disclosure.

The sensor module (520) and the guide needle (550) according to the second embodiment of the present disclosure are formed in structures in which the guide needle (550) surrounds an outside of the sensor probe portion (521) as described above.

In the body insertion process, the guide needle (550) is inserted prior to or at the same time as the insertion of the sensor module (520), and is extracted and removed by the applicator (10) after being inserted into the body. In order for the guide needle (550) to be inserted into the body prior to or at the same time as the insertion of the sensor module (520), an end of the guide needle (550) protrudes further than or as much as an end of the sensor module (520) as illustrated in FIG. 8.

At this time, the guide needle (550) is formed in a shape that surrounds an outside of the sensor probe portion (521) of the sensor module (520), but the guide needle (550) is not formed in a shape of surrounding a whole area of the sensor probe portion (521) from the outside and is formed in a shape of not surrounding at least a part of the sensing area (5211) formed at the sensor probe portion (521) from the outside.

To this end, an opening (EP) may be formed at the end of the guide needle (550) so as not to surround at least a portion of the sensing area (5211) as shown in FIGS. 8 and 9. The opening (EP) may be formed in a shape in which a part of the guide needle (550) is cut and removed, and the opening (EP) may be formed at the incision portion (550a) area formed at the end of the guide needle (550) and may be formed in a shape that the incision portion (550) is enlarged and extended.

For example, as illustrated in FIGS. 8 and 9(a), openings (EP) in shapes of being symmetrical to each other may be formed at end portions of the guide needle (550) in areas facing both side surfaces of the sensor probe portion (521)

of a flat plate shape, respectively. Unlike this, as shown in FIGS. 8 and 9(*b*), an opening (EP) may be formed at an end portion of the guide needle (550) only in an area facing the sensing area (5211) of the sensor probe portion (521). That is, the opening (EP) may be formed only in an area facing one surface of the sensor probe portion (521) in which the sensing area (5211) is formed, and may not be formed in an area facing the other surface of the sensor probe portion (521).

Like this, when the opening (EP) is formed only in the area facing one surface of the sensor probe portion (521) in which the sensing area (5211) is formed, the skin incision function can be performed smoothly by an area of the incision portion (550*a*) where the opening (EP) is not formed during the body skin insertion process of the guide needle (550).

In addition, the opening (EP) may be formed in a shape that does not cover the entire area of the sensing area (5211) as illustrated by a solid line in FIG. 9, and the opening (EP) may be formed in a shape that does not enclose a partial region of the sensing area (5211) as illustrated by a dotted line in FIG. 9.

Because the sensing area (5211) of the sensor module (520) is not covered by the guide needle (550) from the outside by forming the opening (EP) at the guide needle (550), the incised portion (CA) formed by the guide needle (550) is not formed in an area of the body skin (E) adjacent to the sensing area (5211) after the insertion of the body attachable unit (20) to the body skin (E) is completed.

If the incised portion (CA) is not formed in the area adjacent to the sensing area (5211) as described above, the white blood cells (BC) concentrated in the incised portion (CA) do not exist in the area adjacent to the sensing area (5211), and therefore the loss of blood glucose substances caused by the white blood cells (BC) is reduced in the area adjacent to the sensing area (5211), so that the accuracy of a blood glucose measurement value through the sensing area (5211) can be further improved.

Accordingly, as the incised portion (CA) formed by the guide needle (550) is minimized in the adjacent area facing the sensing area (5211), that is, the incised area (CA) formed by the guide needle (550) is located further away from the sensing area (5211), the loss of blood glucose substances by the white blood cells (BC) in the vicinity of the sensing region (5211) decreases, thereby obtaining a more accurate blood glucose measurement value.

As described in FIG. 7, the incised portions (CA) formed by the insertion support portion (550*b*) of the guide needle (550) are formed on both sides of the sensor probe portion (521), and the incised portions (CA) formed by the incision portion (550*a*) of the guide needle (550) are formed to extend in an oblique direction from the end of the incised portion (CA) by the insertion support portion (550*b*) as indicated by a dotted line in FIG. 7.

Accordingly, the incised portion (CA) formed by the insertion support portion (550*b*) is formed to face the sensing area (5211) at an area more adjacent to the sensing area (5211) than the incised portion (CA) formed by the incision portion (550*a*) of the guide needle (550), and therefore the incised portion (CA) formed by the insertion support portion (550*b*) affects more the loss of the blood glucose substance by the white blood cells (BC) in the vicinity of the sensing region (5211). Accordingly, a degree in which the incised portion (CA) formed by the insertion support portion (550*b*) is away from the sensing region (5211) greatly affects the blood glucose measurement accuracy.

In the second embodiment of the present disclosure, because the opening (EP) is formed in the incision portion (550*a*) area of the guide needle (550), an incised portion (CA') is formed to be extended along the shape of the opening (EP) from the end of the incised portion (CA) by the insertion support portion (550*b*) as shown in FIG. 10. The incised portion (CA) by the opening (EP) and the incised portion (CA') by the incision portion (550*a*) are shown by dotted lines in FIG. 10.

For example, if the openings (EP) of the guide needle (550) are formed at portions facing both side surfaces of the sensor probe portion (521) as shown in FIGS. 8(*a*) and 9(*a*), respectively, after the insertion of the body attachable unit (20) to the body skin (E) is completed, the incised portion (CA) by the guide needle (550) is not formed in an adjacent portion of an area facing the sensing portion (5211) as well as an adjacent portion of an area not facing the sensing portion (5211) as illustrated in FIG. 10(*a*). More specifically, the incised portion (CA) by the insertion support portion (550*b*) of the guide needle (550) is not formed in an adjacent region of the sensing portion (5211), and an incised portion (CA') by the opening (EP) is formed to be extended from the end of the incised portion (CA) by the insertion support portion (550*b*) as indicated by a dotted line. Because the opening (EP) is formed in a shape that does not surround the sensing portion (5211), the incised portion (CA') by the opening (EP) does not surround the sensing portion (5211).

If the opening (EP) of the guide needle (550) is formed only in a portion facing one side surface of the sensor probe portion (521) where the sensing portion (5211) is formed as illustrated in FIGS. 8(*b*) and 9(*b*), after the insertion of the body attachable unit (20) to the body skin (E) is completed, the incised portion (CA) by the guide needle (550) is not formed at an adjacent portion of an area facing the sensing portion (5211) (In this case, the incised portion (CA) is formed at a peripheral portion of an area not facing the sensing portion (5211)). More specifically, the incised portion (CA) by the insertion support portion (550*b*) of the guide needle (550) is not formed in an adjacent portion of an area facing the sensing portion (5211), and the incised portion (CA') by the opening (EP) is formed to be extended from the end of the incised portion (CA) by the insertion support portion (550*b*) as shown by a dotted line. Because the opening (EP) is formed in a shape that does not surround the sensing portion (5211), the incised portion (CA') by the opening (EP) does not surround the sensing portion (5211). Of course, an incised portion (CA) by the insertion support portion (550*b*) is formed at a peripheral portion of an area that does not face the sensing portion (5211), and the incised portion (CA) by the incision portion (550*a*) is formed to be extended from its end as illustrated by a straight path of a dotted line.

Schematically, as shown in FIG. 10, the insertion depth of the sensor module (520) is SD, the insertion depth of an end of the guide needle (550) is formed to be ND deeper than SD, and the incised portion (CA) by the guide needle (550) is formed to have the same depth ND as the insertion depth of the guide needle (550).

In the state of FIG. 10(*a*), the depth of the incised portion (CA) by the insertion support portion (550*b*) of the guide needle (550) is ND1 shallower than SD, and in particular, the depth ND1 of the incised portion (CA) is a depth shallower than the sensing portion (5211). In the state of FIG. 10(*b*), the depth of the incised portion (CA) by the insertion support portion (550*b*) of the guide needle (550) is ND1 in an area facing the sensing portion (5211) and ND2 in an area not facing the sensing portion (5211). In this case, ND2 may be formed to be deeper than SD, but ND1 is formed to be shallower than SD and is formed to be shallower than the sensing region (5211) like FIG. 10(*a*).

Because the absence of the incised portion (CA) at an adjacent portion of an area facing the sensing portion (5211) has a greater effect on improving blood glucose measurement accuracy, the incised portion (CA) is not formed by the opening (EP) in the peripheral portion of the area facing the sensing portion (5211), and therefore loss of blood glucose substances by the white blood cells (BC) can be prevented, thereby improving blood glucose measurement accuracy.

Accordingly, by a structure that the guide needle (550) is formed so as not to surround the sensing portion (5211) from the outside by the opening (EP), the incised portion (CA) by the guide needle (550) has a shape not surrounding the sensing portion (5211) from the outside, and accordingly, the blood glucose measurement accuracy for the sensing portion (5211) can be further improved by minimizing a phenomenon of decrease in blood glucose substances occurring at the incised portion (CA) due to the white blood cells (BC).

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. A continuous glucose measurement apparatus comprising:

a body attachable unit configured to be insertedly attachable to a body by an applicator and periodically measure blood glucose; and wherein the body attachable unit comprises:

a sensor module configured to be insertable to the body, and a guide needle comprising a first side and a second side to cover an outside of at least a partial area of the sensor module, and configured to guide insertion of the sensor module to the body and to, after linearly moving integrally together with the sensor module, be extracted and removed from the body, wherein an end of the guide needle is arranged to protrude further than an end of the sensor module toward a body insertion direction or protrude as much as the end of the sensor module, wherein the sensor module comprises:

a sensing area to react with the blood glucose in the body, wherein a first surface of the sensor module faces the first side of the guide needle, and a second surface of the sensor module faces the second side of the guide needle, wherein the sensing area is formed at an end part and on the first surface of the sensor module, wherein the guide needle comprises a longitudinal channel opened along the longitudinal direction and disposed between the first side and the second side, and wherein the guide needle comprises a cutout portion only formed at the end portion of the first side of the guide needle in an area facing the sensing area not to cover the at least a partial area of the sensing area of the sensor module.

2. The continuous glucose measurement apparatus of claim 1, wherein the sensor module comprises a sensor probe portion formed to be elongated along the body insertion direction so that at least a partial section of the sensor probe portion is insertable into the body, and the sensing area is formed at an end part of the sensor probe portion.

3. The continuous glucose measurement apparatus of claim 2, wherein the guide needle is formed to have a shape of covering an outside of the sensor probe portion.

4. The continuous glucose measurement apparatus of claim 3, wherein the sensor probe portion is formed to have a plate shape elongated along the body insertion direction, the sensing area is formed at one surface of the sensor probe portion, and the cutout portion of the guide needle is formed to have an opened shape in which an area of the guide needle facing the one surface of the sensor probe portion at which the sensing area is formed is opened.

5. The continuous glucose measurement apparatus of claim 3, wherein an incised portion formed by the cutout portion does not cover the sensing area.

6. The continuous glucose measurement apparatus of claim 1, wherein the cutout portion of the guide needle is formed to have a shape of not covering an entire area of the sensing area.

7. The continuous glucose measurement apparatus of claim 1, wherein the cutout portion of the guide needle is formed to have a shape of not covering the partial area of the sensing area.

8. The continuous glucose measurement apparatus of claim 1, wherein the guide needle comprises:

an incision portion formed at a front end portion of the guide needle to incise skin of the body in a process in which the guide needle is being inserted into the body, and an insertion support portion formed to be extended from a back portion of the incision portion and configured to be inserted to the body continuously along an incised portion incised by the incision portion, and wherein the cutout portion is formed at an area of the incision portion.

9. The continuous glucose measurement apparatus of claim 1, wherein the guide needle comprises a second cutout portion formed on the second side to form symmetry.

* * * * *